(12) United States Patent
Dooley et al.

(10) Patent No.: US 9,702,860 B2
(45) Date of Patent: Jul. 11, 2017

(54) DEVICE FOR MONITORING WASTEWATER TREATMENT

(71) Applicant: Strathkelvin Instruments Limited, North Lanarkshire (GB)

(72) Inventors: Michael Anthony Dooley, West Lothian (GB); Martin Burns, North Lanarkshire (GB)

(73) Assignee: Strathkelvin Instruments Limited, North Lanarkshire (GB)

( * ) Notice: Subject to any disclaimer, the term of this patent is extended or adjusted under 35 U.S.C. 154(b) by 83 days.

(21) Appl. No.: 14/431,545

(22) PCT Filed: Sep. 30, 2013

(86) PCT No.: PCT/GB2013/052537
§ 371 (c)(1),
(2) Date: Mar. 26, 2015

(87) PCT Pub. No.: WO2014/049376
PCT Pub. Date: Apr. 3, 2014

(65) Prior Publication Data
US 2015/0241402 A1    Aug. 27, 2015

(30) Foreign Application Priority Data
Sep. 28, 2012 (GB) .................................. 1217350.6

(51) Int. Cl.
*G01N 33/18* (2006.01)
*G01N 15/06* (2006.01)

(52) U.S. Cl.
CPC ............. *G01N 33/18* (2013.01); *G01N 15/06* (2013.01); *G01N 33/1806* (2013.01); *C02F 2209/00* (2013.01); *C02F 2209/22* (2013.01)

(58) Field of Classification Search
CPC .... G01N 33/18; G01N 15/06; G01N 33/1806; C02F 2209/00; C02F 2209/22
(Continued)

(56) References Cited

U.S. PATENT DOCUMENTS 4,260,490 A * 4/1981 Moss ................. G01N 33/1806
210/195.3
4,330,385 A * 5/1982 Arthur ............... G01N 33/1806
204/409

(Continued)

FOREIGN PATENT DOCUMENTS

WO    2009067504 A2    5/2009

OTHER PUBLICATIONS

International Search Report and Written Opinion dated Jan. 17, 2014 for PCT/GB2013/052537.

*Primary Examiner* — Hezron E Williams
*Assistant Examiner* — Marrit Eyassu
(74) *Attorney, Agent, or Firm* — Abel Law Group, LLP

(57) ABSTRACT

Disclosed is a wastewater monitoring device comprising, a selectively sealable chamber; a first oxygen sensor, operable to measure the level of oxygen dissolved in a liquid; said first oxygen sensor being locatable inside of the sealed sealable chamber; and a second oxygen sensor, operable to measure the level of oxygen dissolved in the wastewater being tested. The selectively sealable chamber may be defined by a shell member and a piston member, the piston being locatable inside the shell member so as to define said chamber. At least one of the shell member and piston member may be actuatable linearly relative to the other so as to selectively seal the chamber.

20 Claims, 9 Drawing Sheets

(58) Field of Classification Search
USPC .......................................................... 73/61.71
See application file for complete search history.

(56) References Cited

U.S. PATENT DOCUMENTS

| | | | |
|---|---|---|---|
| 4,846,965 A * | 7/1989 | Clifft | ...................... C02F 3/006 210/110 |
| 5,233,860 A | 8/1993 | Mori et al. | |
| 5,531,960 A | 7/1996 | Zelinka | |
| 5,976,888 A * | 11/1999 | Lee | ................... G01N 33/0037 210/614 |
| 6,063,617 A | 5/2000 | Young et al. | |
| 2007/0175823 A1 * | 8/2007 | Cheuk | ..................... C02F 3/006 210/614 |
| 2010/0332149 A1 | 12/2010 | Scholpp | |
| 2012/0006414 A1 * | 1/2012 | Hazard | ................... C02F 3/006 137/4 |

* cited by examiner

DEVICE FOR MONITORING WASTEWATER TREATMENT

The present invention relates to wastewater treatment and in particular to monitoring devices used in wastewater treatment facilities.

Wastewater treatment plants (WWTP) are presently often very inefficient. Many use simple devices for measuring dissolved oxygen (DO) in the wastewater. DO is a standard measurement on all biological wastewater treatment plants. It is used to control how hard the air system is driven to supply air so that the DO reaches a target set point, while the bacteria consume the oxygen supplied. Too much DO and energy is wasted, too little and the incoming materials may not completely biodegrade and the formation of undesirable bacterial species may be encouraged, causing treating plant problems.

As a "rule of thumb", DO is kept usually maintained roughly around 2-2.5 mg/l. To monitor the DO level, luminescence oxygen sensors are often used. However, their maintenance can be a problem, due to problems such as the sensors becoming soiled, or covered with debris. They can also be difficult or time consuming to calibrate.

It would be desirable to address one or more of these issues.

In a first aspect of the invention there is provided a wastewater monitoring device comprising:
a selectively sealable first chamber;
a first oxygen sensor, operable to measure the level of oxygen dissolved in a liquid;
said first oxygen sensor being locatable inside of the sealed first chamber;
a second oxygen sensor, operable to measure the level of oxygen dissolved in the wastewater being tested.

Said device may be operable to perform a low point calibration operation, comprising calibrating said first oxygen sensor within the sealed first chamber under controlled conditions. High point calibration of said first oxygen sensor may be performed by exposing the system to air under controlled conditions.

To calibrate the second oxygen sensor, said calibration operation may comprise deploying the second sensor in a sealed calibration second chamber under controlled conditions for the lower point calibration and calibrating the high point by automatically exposing the sensor to air under controlled conditions.

To calibrate both oxygen sensors, said calibration operation may comprise: sealing a sample of the wastewater and said first oxygen sensor within the chamber; allowing the bacteria to consume all available oxygen and then determining that the level of dissolved oxygen is constant over time using said first oxygen sensor and, when constant, calibrating the said first oxygen sensor at zero.

To calibrate the both oxygen sensors, said calibration may further comprise measuring the level of dissolved oxygen in air using said first oxygen sensor and using this measure as a high point calibration value.

Said selectively sealable chamber(s) may be defined by a shell member and a piston member, the piston being locatable inside the shell member so as to define said chamber(s); at least one of said shell member and piston member being actuatable linearly relative to the other so as to selectively seal the chamber(s).

Said device may be operable such that each of said shell member and said piston member can be independently actuated relative to the other. Said device may comprise a first actuator for the shell member and a second actuator for the piston member.

Said device may be operable in at least three configurations, a first configuration in which the piston member is withdrawn relative to the shell member thereby allowing the ingress of surrounding liquid, a second configuration wherein said piston member is deployed relative to the shell member so as to contain said liquid and said oxygen sensor within said first chamber, and a third configuration wherein said piston member is deployed further relative to the shell member, so as to expel the contained liquid from said first chamber.

Said device may comprise one or more wiping elements for wiping one or more of the sensor surfaces. Said wiping elements may be located such that said sensors are wiped during actuation of either or both of said shell member and said piston member.

Said device may comprise agitation means for agitating a liquid sample contained within said first chamber. Said agitation means may comprise a stirrer. Said stirrer may be operable to cut up any debris material which enters the first chamber. Said device may comprise oxygenating means for oxygenating a liquid sample contained within said first chamber.

Said device may comprise a solids sensor operable to measure a level of suspended solids within a sample. Said system may be operable to contain a liquid sample into the device's first chamber and to perform a settled volume index measurement. This measurement may comprise measuring settled levels and supernatant levels. Said measurement may comprise determining a percentage of full sample height at which a sudden increase in solids is detected. Said device may be further operable to stir the sample and perform a stirred settled volume index measurement.

Said system may be further operable to contain a liquid sample in the device's first chamber and to perform a mixed liquor suspended solids measurement. Said system may also be operable to contain a liquid sample into the device's first chamber, allow the sample to settle over a predetermined time and to perform a total suspended solids measurement.

Said device may comprise one or more of: a temperature sensor, a pH sensor, an ammonia sensor and a potassium sensor.

Said device may comprise a sealed calibration housing and a reservoir for calibration fluids, and being operable to: withdraw one or more sensors, other than the first oxygen sensor, into the calibration housing, filling the calibration housing with calibration fluids, and calibrated the sensor(s) using said calibration fluids.

Said device may comprise an outer casing having an open end through which the piston member and/or the shell member can be deployed and withdrawn. In an embodiment the open end of the casing comprises a sharp edge and/or deflector to prevent debris fouling the device.

Said device may be operable to pressurise inlet holes to said first chamber.

In a further aspect of the invention there is provided a wastewater monitoring system comprising at least one wastewater monitoring device of the first aspect; and a controller.

Said system may be operable to measure the oxygen uptake rate of a liquid sample contained within the sealed first chamber of the device. To do this, said system may be operable to:
seal a sample of the wastewater and said first oxygen sensor within the first chamber of the device;

oxygenate the sample to raise the level of dissolved oxygen within it;
determine the rate of change of the dissolved oxygen level over time.

Said system may be operable to plot the change in oxygen uptake rate against the concentration of dissolved oxygen so as to determine an optimum operating dissolved oxygen concentration range. To do this said system may be operable to determine a Critical Carbonaceous point at which decreasing dissolved oxygen concentration results in a sharp fall in the oxygen uptake rate. Said system may be further operable to determine a Critical Nitrification point where increasing dissolved oxygen concentration begins to have very little or no effect on the oxygen uptake rate, this being indicative of the point at which dissolved ammonia removal rates is considered to be maximised. A dissolved oxygen range can then be chosen which provides the best compromise of organic compound removal, ammonia removal and energy efficiency.

Said system may be further operable to perform an online toxicity assessment of the wastewater under test. Said system may be operable to use a decision matrix to attribute a toxicity value based upon the level of a number of parameters, and summing the attributed toxicity values to provide a toxicity score indicating the level of toxicity of the sample. The parameters may include oxygen uptake rate, percentage nitrification and ammonia reduction rate.

Said system may comprise a plurality of devices of the first aspect of the invention and said controller may be operable to feed forward and/or feedback measurement data as appropriate. In a specific embodiment the system may be operable to measure an incoming load, determine load removal rates and the required dissolved oxygen levels to achieve this, monitor the correct treatment conditions in the treatment system, measure effluent load and feedback results to the controller.

Also described is a wastewater monitoring device comprising:
a selectively sealable first chamber;
an oxygen sensor, operable to measure the level of oxygen dissolved in a liquid; said oxygen sensor being locatable inside of the sealed first chamber;
wherein said selectively sealable first chamber is defined by a shell member and a piston member, the piston being locatable inside the shell member so as to define said first chamber; at least one of said shell member and piston member being actuatable linearly relative to the other so as to selectively seal the first chamber.

Said device may be operable such that each of said shell member and said piston member can be independently actuated relative to the other. Said device may comprise a first actuator for the shell member and a second actuator for the piston member.

Said device may be operable in at least three configurations, a first configuration in which the piston member is withdrawn relative to the shell member thereby allowing the ingress of surrounding liquid, a second configuration wherein said piston member is deployed relative to the shell member so as to contain said liquid and said oxygen sensor within said first chamber, and a third configuration wherein said piston member is deployed further relative to the shell member, so as to expel the contained liquid from said first chamber.

Said device may comprise one or more wiping elements for wiping at least said first sensor surfaces. Said wiping elements may be located such that said sensor is wiped during actuation of either or both of said shell member and said piston member.

Said device may comprise agitation means for agitating a liquid sample contained within said first chamber. Said agitation means may comprise a stirrer. Said stirrer may be operable to cut up any debris material which enters the first chamber. Said device may comprise oxygenating means for oxygenating a liquid sample contained within said first chamber.

Said device may comprise a solids sensor operable to measure a level of suspended solids within a sample. Said system may be operable to contain a liquid sample into the device's first chamber and to perform a settled volume index measurement. This measurement may comprise measuring settled levels and supernatant levels. Said measurement may comprise determining a percentage of full sample height at which a sudden increase in solids is detected, calculated using the known distance between piston and solid sensor. Said device may be further operable to stir the sample and perform a stirred settled volume index measurement.

Said system may be further operable to contain a liquid sample into the device's first chamber and to perform a mixed liquor suspended solids measurement. Said system may also be operable to contain a liquid sample into the device's first chamber, allow the sample to settle over a predetermined time and to perform a total suspended solids measurement.

Said device may comprise one or more of: a temperature sensor, a pH sensor, an ammonia sensor and a potassium sensor.

Said device may comprise a sealed calibration housing and a reservoir for calibration fluids, operable such that one or more sensors, other than the first oxygen sensor, are withdrawn into the calibration housing, which is then filled with calibration fluids so that the sensor(s) may be calibrated.

Said device may comprise an outer casing having an open end through which the piston member and/or the shell member can be deployed and withdrawn. In an embodiment the open end of the casing comprises a sharp edge and/or deflector to prevent debris fouling the device.

Said device may be operable to pressurise inlet holes to said first chamber.

In a further aspect of the invention there is provided method of calibrating a wastewater monitoring device comprising:
sealing a first sample of wastewater and a first oxygen sensor within a first chamber;
sealing a second sample of wastewater and a second oxygen sensor within a second chamber;
oxygenating each of said first and second samples to raise the level of dissolved oxygen within it;
determining that the level of dissolved oxygen is constant over time in said first sample using said first oxygen sensor, and when constant, calibrating the said first oxygen sensor at zero;
determining that the level of dissolved oxygen is constant over time in said second sample using said second oxygen sensor, and when constant, calibrating the said second oxygen sensor at zero.

Said method may further comprise making a comparison the determinations made using said first oxygen sensor and said second oxygen sensor so as to determine whether they corroborate.

Said method may further comprise measuring the level of dissolved oxygen in air using said first oxygen sensor and said second oxygen sensor using these measurements as a high point calibration value for the first oxygen sensor and said second oxygen sensor, respectively.

In a further aspect of the invention there is provided a method of performing an online toxicity assessment of wastewater comprising: using a decision matrix to attribute a toxicity value based upon the level of a number of parameters, and summing the attributed toxicity values to provide a toxicity score indicating the level of toxicity of the sample. The parameters may include oxygen uptake rate, percentage nitrification and ammonia reduction rate.

BRIEF DESCRIPTION OF THE DRAWINGS

Embodiments of the invention will now be described, by way of example only, by reference to the accompanying drawings, in which.

DETAILED DESCRIPTION OF THE EMBODIMENTS

Figure 1:
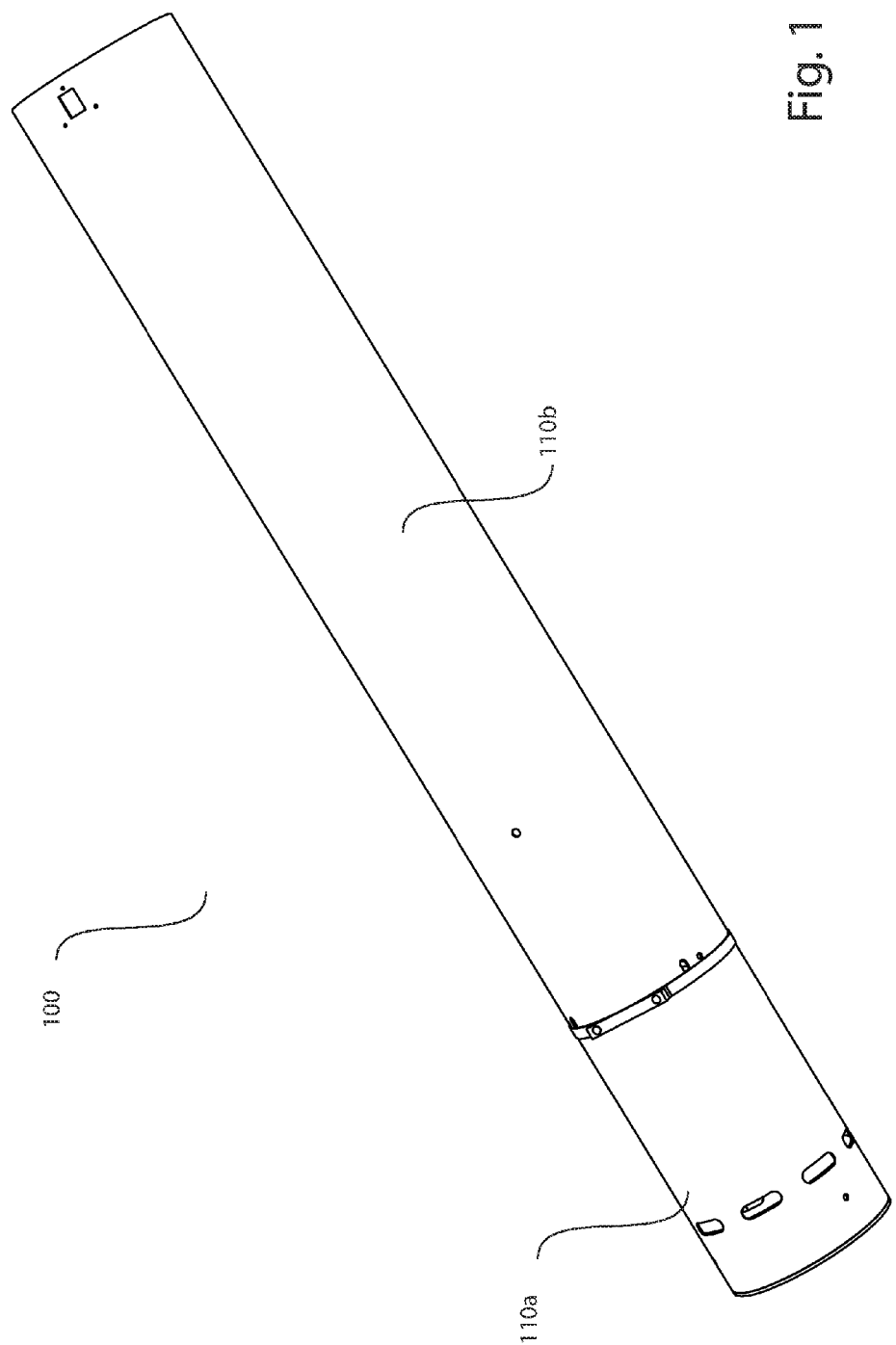
FIG. 1 shows a device for wastewater treatment monitoring according to an embodiment of the invention.
Figure 2:
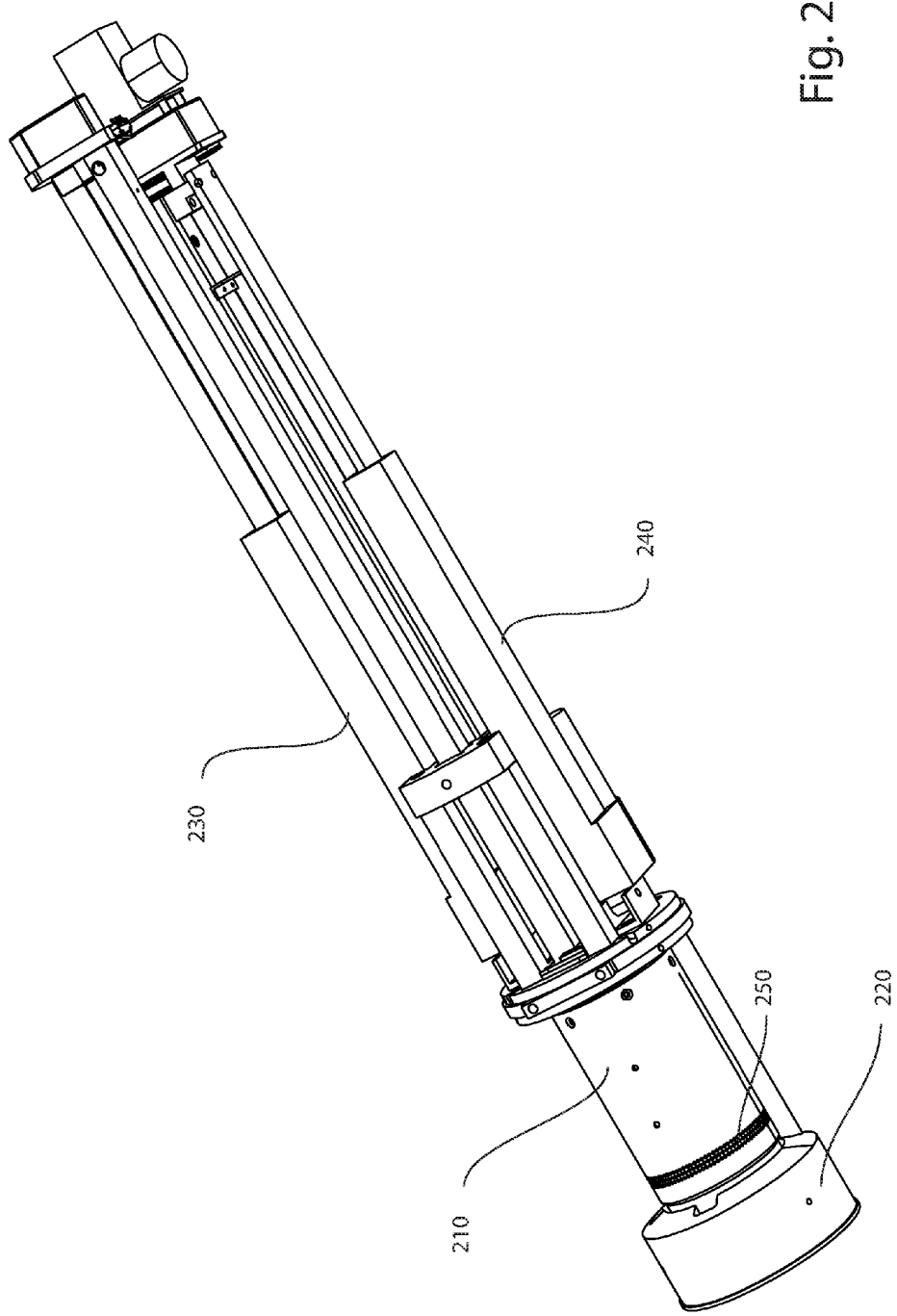
FIG. 2 shows the device of FIG. 1, with outer casing removed, in a first configuration.

FIGS. 1 and 2 show a device 100 for the monitoring and control of Biological Wastewater Treatment Facilities, with outer casing 110a and 110b and without outer casing 110a and 110b respectively. In FIG. 2, the respiration chamber shell 210, static top assembly 220, shell actuator 230 for actuating the shell 210, and piston actuator 240 for actuating the piston and internal sensor assembly inside of shell 210. The shell comprises inlet sample holes 250 to allow liquid samples to be taken inside of the shell. The device is shown here in its fully retracted configuration. This configuration forms a sealed chamber within which certain tests may be carried out.

Figure 3:
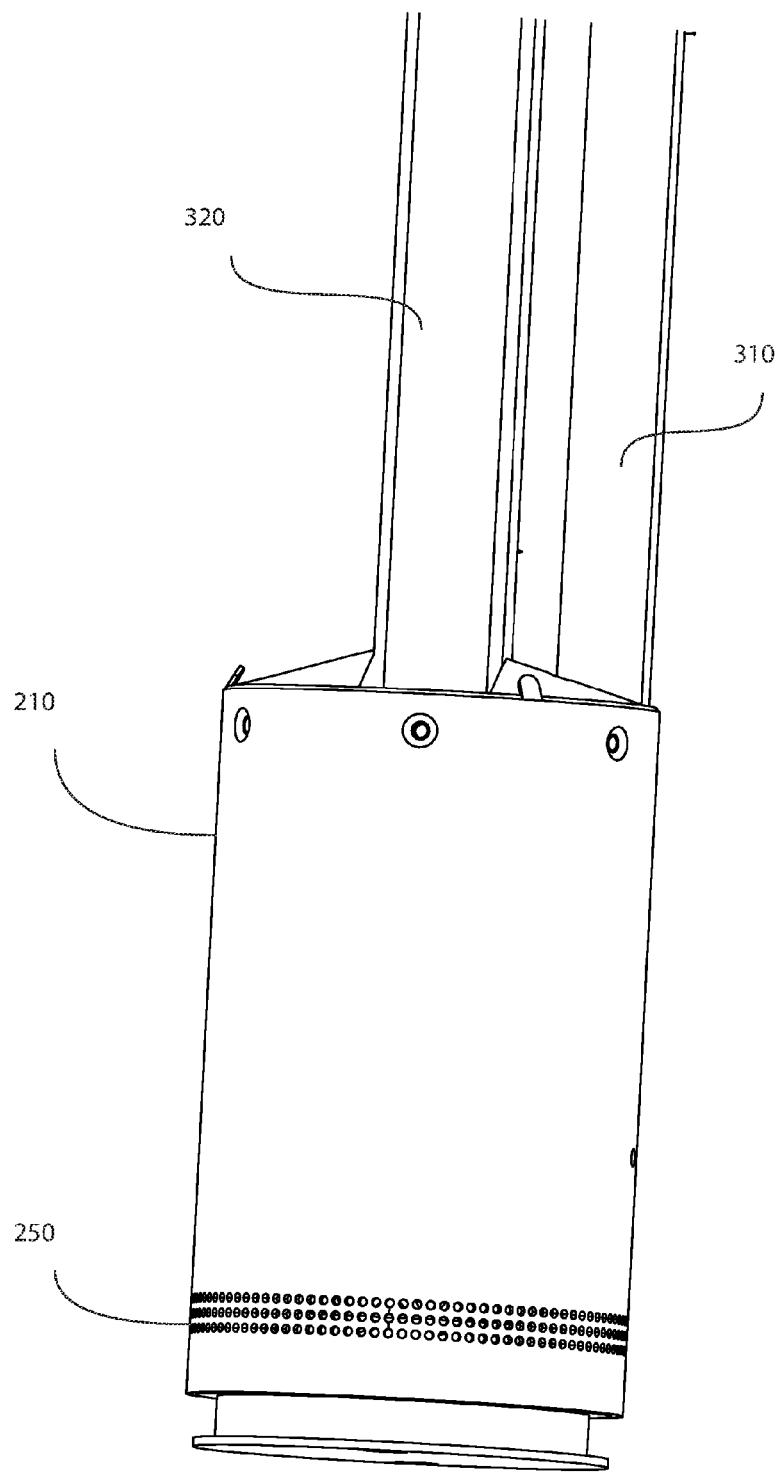
FIG. 3 shows a detail of the respirometry chamber of the device of FIG. 1 in said first configuration.
Figure 4:
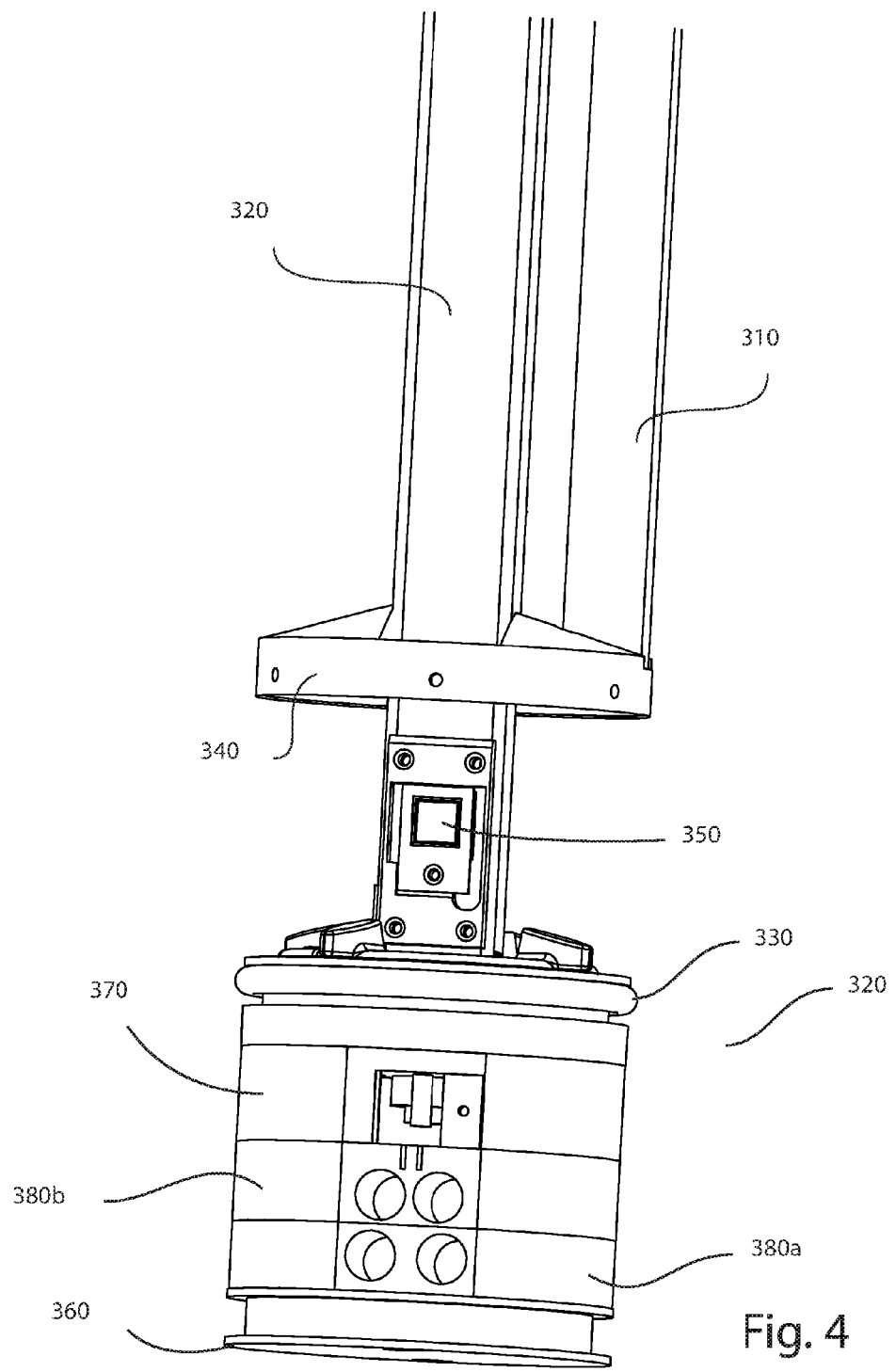
FIG. 4 shows a detail of the respirometry chamber of the device of FIG. 1 in said first configuration, with the chamber shell removed.

FIGS. 3 and 4 show a detail of the sensing end of the device 100, with shell 210 in place and removed respectively. Shown are shell actuating arm (part of) 310, central assembly (part of) 320, which acts as the actuating arm for piston assembly 320. The piston assembly comprises seal 330 which seals against the inside of shell 210 thereby providing for a sealed chamber when the device is in this particular configuration, the chamber defined by the shell 210, shell end piece 340, and piston assembly 320. Shell end piece 340 may comprise a fluid vent chamber, a wiper for the internal DO sensor and a solids sensor (e.g. an optical solids sensor). Inside of this respiration chamber is an internal dissolved oxygen (DO) sensor 350 (here attached to the central assembly/actuating arm 320. Also shown is a housing for an external DO sensor 370, and housings 380a, 380b for other sensors. Other sensors may comprise inter alia: a temperature sensor, a pH sensor, sensors for other chemicals e.g. ammonia, or potassium, or a solids sensor.

Of particular note is that the shell 210 and piston assembly 320 are capable of independent lateral (along the major axis of the device) movement and control. The movement of both these components is capable of being very tightly controlled, as the relative positions of these components allow unique measurements to be carried out and significantly improves the reliability of the equipment. The relative movement, and the capability to measure exactly where each component is, enables the following:

Automatic Calibration of all sensors.
Sensor head cleaning.
Rag Handling.
Settlement tests.
Respirometry runs.

Figure 5:
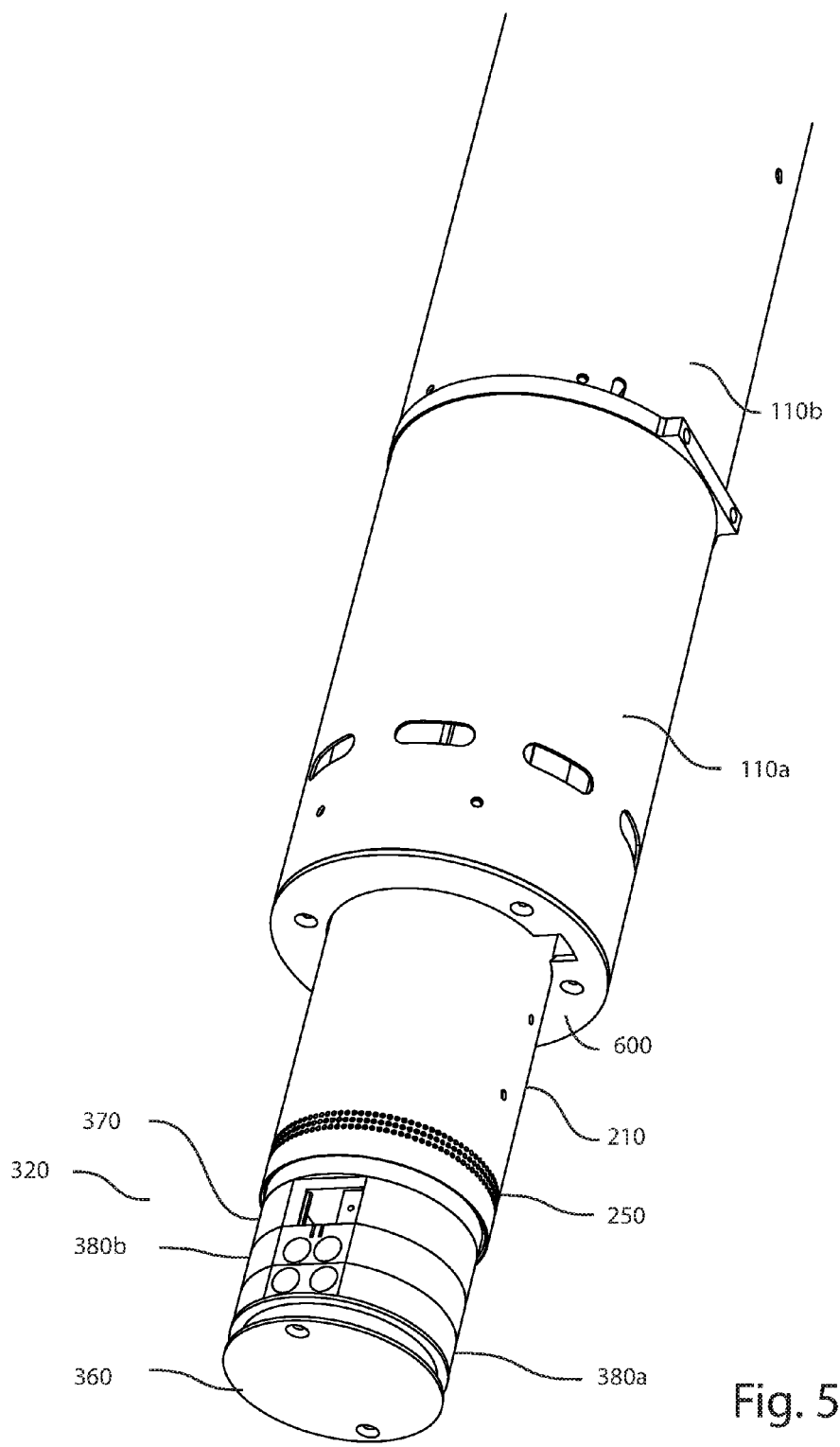
FIG. 5 shows a detail of the respirometry chamber of the device of FIG. 1 in a second configuration.

FIG. 5 shows the device 100 in its filling configuration. Piston assembly 320 has been extended such that its seal 330 (FIG. 4) is beyond filling holes 250. Liquids under test can then enter the respirometry chamber through these holes 250. The device can then be put into its retracted position (FIGS. 1 to 4) by moving either or both of the shell 210 and piston assembly 320 such that the seal 330 is no longer beyond filling holes 250, thereby capturing the liquid inside the respirometry chamber.

Figure 6A:
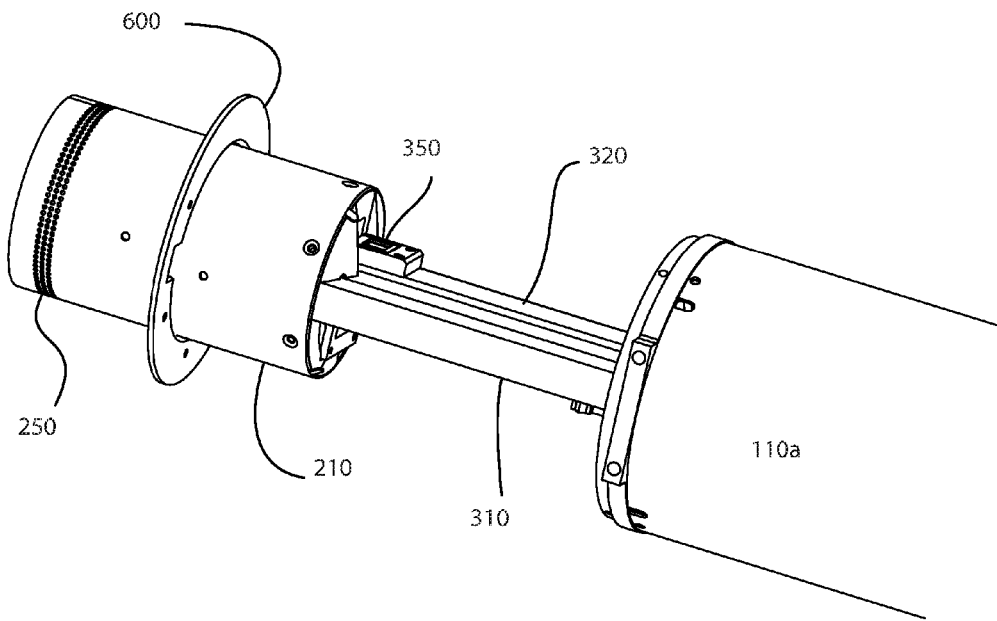
FIGS. 6a and 6b shows a detail of the respirometry chamber of the device of FIG. 1 in a third configuration, respectively with the chamber shell shown and with the chamber shell removed.
Figure 6B:
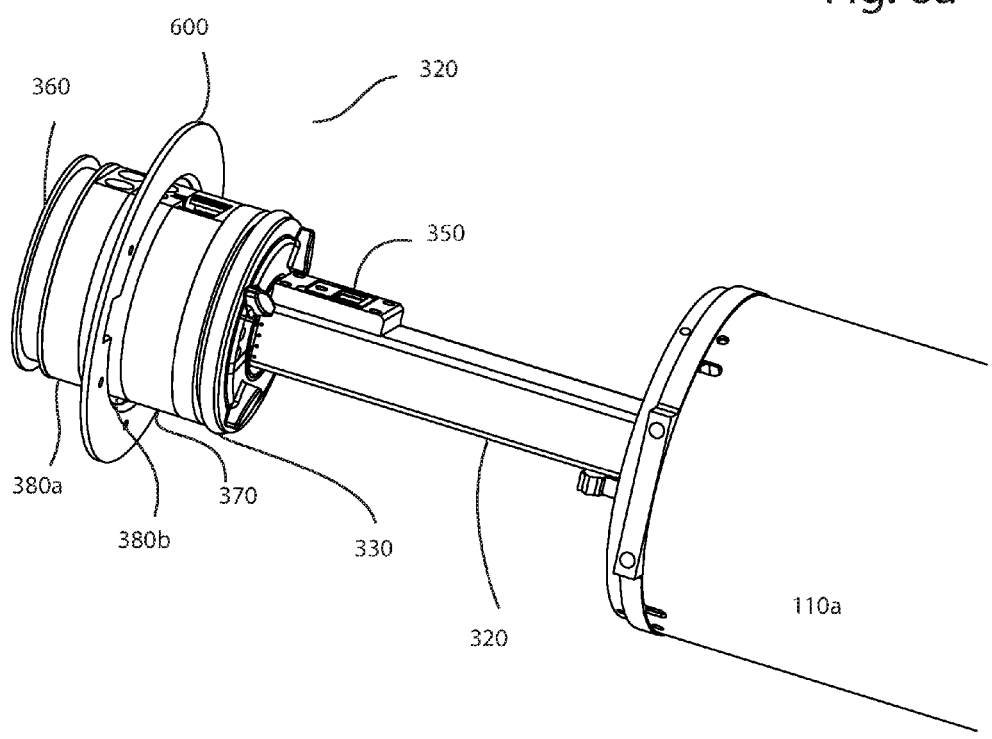

FIGS. 6a and 6b show the device in its expelled configuration, immediately after the expulsion of liquids from the respirometry chamber. For clarity, outer casing section 110a and static top assembly 220 are not shown. FIG. 6a shows the configuration with the shell 210 shown, and FIG. 6b shows the configuration with the shell 210 not shown. End ring 600 is shown to indicate the position of the casing 110a end. As can be seen, the piston assembly 320 is at the bottom of the shell 210. The liquids are expelled through the fluid vent chamber 340. Also of note is that internal DO sensor 350 is now instrument air space, within the device casing, and is being wiped clean by wiper.

Figure 7A:
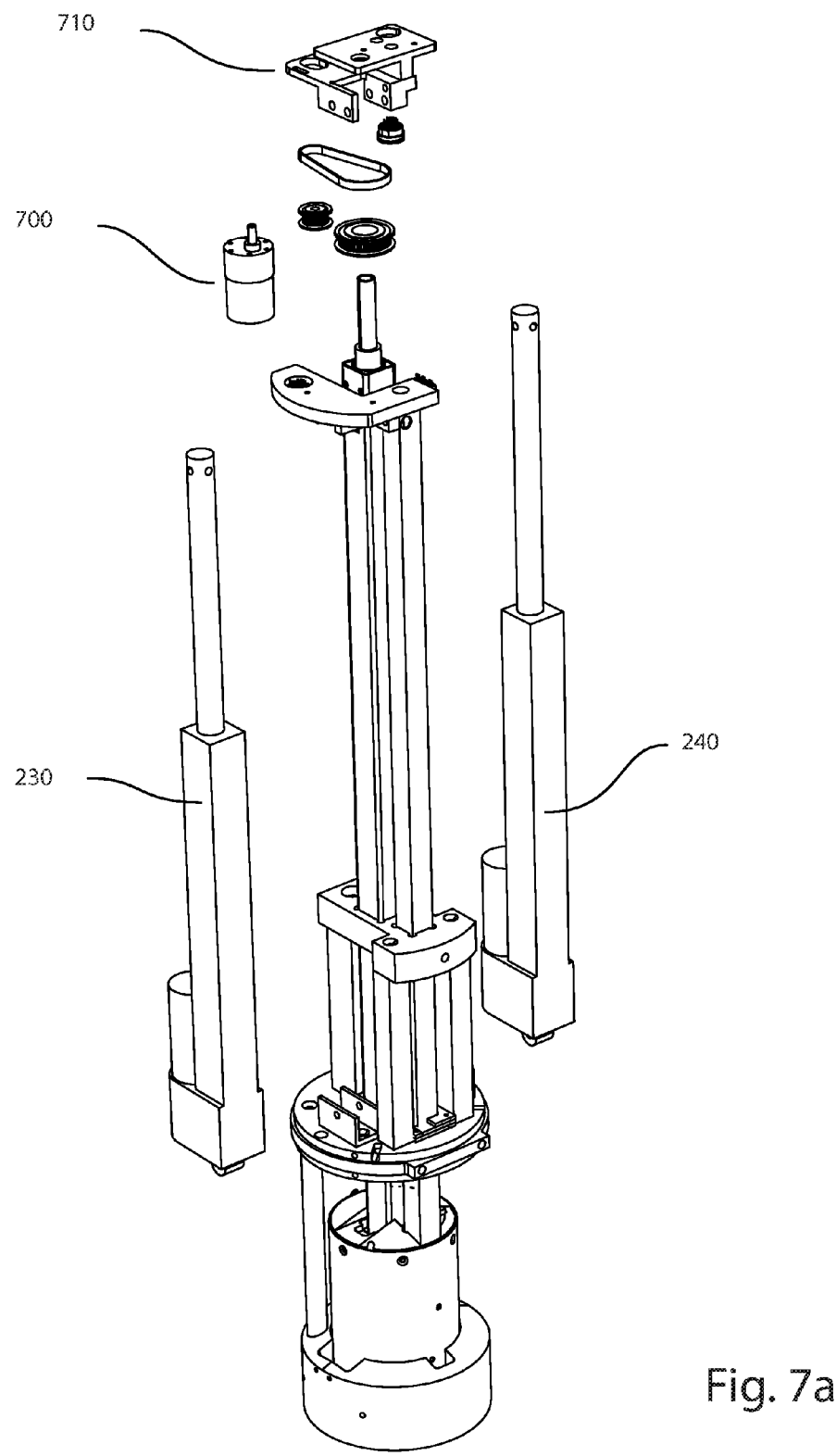
FIGS. 7a and 7b are blown up views of the device of FIG. 1.
Figure 7B:
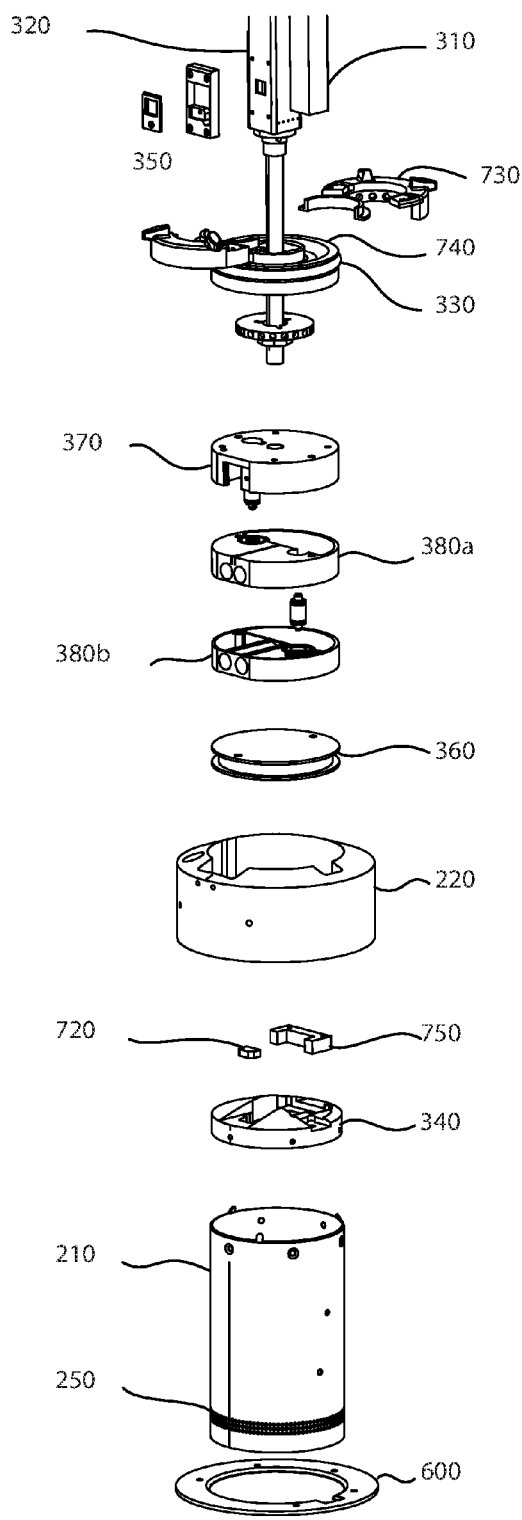

FIGS. 7a and 7b show the top section and bottom section of the device 100, blown up. In addition to the already described elements, shown are: motor and motor drive 700, top bracket 710, wiper device 720, internal stirrer 730, magnetic drive for mixer 740 and solid sensor 750.

Respirometry and Calibration Using Dissolved Oxygen Sensors

The internal DO sensor 350, inside of the respiration chamber, is used to measure the respiration rate of a captured mixed liquor sample. Depending on where the instrument is located this measure can tell the Plant Operator:

Influent loading levels (when located at inlet)
Percent Treatment completion (when located further down treatment system)

The sample is grabbed from the basin and may be agitated in the sealed internal respiration chamber by an internal agitation device, such as a stirrer. The internal chamber may be provided with a self-contained aeration device to allow the DO level to be raised sufficiently for accurate determination during the respiration run of (for example):

Oxygen Uptake Rate (OUR)
Critical DO for carbon removal
Critical DO for Ammonia Removal
% Nitrification Activity Once the DO level has been raised sufficiently the aeration is switched off and the rate of OUR decay in the chamber is measured. This is taken to be the Oxygen Uptake Rate (OUR). When the respiration run is complete the internal sample will be at zero DO. In reality, the reading may be slightly higher than zero, but the instrument will sense that the reading is not changing. If so, the internal sensor can be calibrated at zero.

At a later stage in the instrument operating cycle the internal DO sensor 350 may be drawn up into the instrument air space immediately above the liquid (therefore at same temperature and pressure) and a high point calibration is completed. The sensor head may also be wiped clean by wiper during this process These calibration steps are carried out without interrupting the dissolved oxygen measurement in the liquid under test, using the external DO sensor (within housing 370). The external DO sensor is kept in the plant mixed liquors continuously. It is routinely cleaned by a further wiper-blade and at automatic, pre-determined intervals; or under manual instruction from an operator.

In one embodiment the external DO sensor may be calibrated using the internal DO sensor, once the latter is fully cleaned and calibrated as described above. Internal DO sensor 350 and external DO sensor are immersed in the mixed liquors, ideally in close proximity to each other. The calibration curve for the uncalibrated external LDO sensor is then adjusted to match the readings of the calibrated internal LDO sensor 350.

A shown in the illustrated embodiment, the external DO sensor may be sealable within its own sealed chamber for calibration. The chamber for the external DO sensor is defined by seals 330, and shell 210. In this embodiment, the external DO sensor is moved by the combined actuated action of piston 320 and shell 210 so that space between seal 330 and seal 360 is filled with mixed liquor solution. A further actuator movement seals the mixed liquor in the chamber with the external DO sensor and the mixed liquor which is allowed to respire. With the external DO sensor within this chamber, low point and high point calibrations can be performed in a manner essentially similar to that described above in relation to the internal DO sensor 350.

The device may be operable to compare the results of the self-calibrations performed by the internal DO sensor 350 and external DO sensor (such as the sealed low point and high point calibrations described). Should they not corroborate, then it may be that one (or both) of the sensors are malfunctioning or that false readings were taken for another reason. Corrective action can then be taken, if deemed necessary.

The LDO sensing heads are replaceable units and can be changed by simply loosening a clamping screw Self-Calibration of Other Sensors Calibration of the other sensor heads, such as those in housings 380*a*, 380*b* can also be self-calibrated in-situ. The relative movements of the various parts of the system allow the sensors to be withdrawn (while being cleaned) into a sealed calibration housing. Calibration fluids are drawn automatically from a reservoir into the calibration housing and the sensors are automatically calibrated.

Self Cleaning of Device Sensors

One or more wiper devices, such as wiper 720 may be provided in order to self-clean any one or more of the device sensors. In an embodiment, these are located in positions such that the movement of the piston assembly 320 or shell 210 assembly between operational configurations cause the sensors to pass and be wiped clean by the wipers.

Rag Handling

Ragging is a serious problem in wastewater treatment plants as the rag (a term used for larger items of debris in the water being tested) wraps around components, causes false measurements and can damage the instrumentation. The capability to withdraw the shell 210 and internal piston 320 completely inside of top assembly 220 wipes the rags off the instrument. As the piston 320 draws into the shell 210, and the shell draws into the deflector plate (which may form part of top assembly) 220, sharp edges may be provided to chop off any adhering rag and prevent significant fouling. The inlet sample holes 250 may be small so as to avoid rag ingress into the internal equipment, and the action of the internal stirrer may be designed to chop off/up any materials which may enter, and may also have sharp edges. The unit may also be designed to have a pulsing vertical motion to pressurise the inlet holes.

Solids Sensor

The device may comprise a solids sensor, which in an embodiment sits in the exhaust port for the trapped mixed liquor sample, used in the respirometry run. It may be set up so that it can measure both high solids level (1,000 mg per liter-20,000 mg/l) and low solids (0-100 mg/l) very accurately. The accuracy of the solids sensor can be improved even further by following a simple calibration process to the actual treatment plant sludge.

When the grab sample is ejected without a settlement phase, the sensor will measure the MLSS (Mixed Liquor Suspended Solids) or quantity of treatment bacteria in the system. Critically every single plant measures this value on an almost daily basis—(normally manually, requiring about 30 minutes of operator time). MLSS is a measure of the amount of bacteria in the system and operators are normally given a target range in which they are required to run the plant. This is set either at commissioning or on an ongoing basis by process engineers. If they go below target, they reduce wasting rates and if they go above the increase wasting rates—(Note wasting is removal of bacteria solids from the recycled activated sludge stream). The target MLSS is normally a function of whether the plant is required to nitrify or not, F:M ratio (Food to Mass ratio)—F:M=BOD influent/MLSS.

When the grab sample is ejected subsequent to a 30-minute (variable) time period the system will initially measure the clarified liquor TSS (giving an indication of discharge TSS— total suspended solids) and then finally will determine the settled (Return Activated Sludge-RAS) solids concentration. It is suggested that TSS projections are carried out on grab samples from near the end of the treatment system.

TSS is a measure of Total Suspended Solids in the effluent. Most plants use this as a compliance consent measurement. Most plants test for this manually (requiring about 30 minutes of operator time) and some have on-line systems to measure it. In an embodiment, the device 100 is not used to measure this in the discharge liquor but instead to predict what it will be by testing the solids level in the settled effluent. This TSS prediction is a measure of how turbid the discharge liquors may be from the final clarifiers (also known as FST—Final Settlement Tanks). This information can be used (possibly in conjunction with SVI/SSVI measurements—described below) in order to determine how the FST tanks should be operated, thereby allowing operators to change settings in the clarifier in advance of a problem occurring.

Some plants have tertiary filters or even membranes prior to discharge and the TSS predictor could be used to determine how much (if any) flow should be diverted to these units, which are highly expensive to operate.

The proposed system is unique in that the same sensor is used to determine normal mixed liquor suspended solids and the actual concentration of these solids (i.e. RAS) once it has settled.

Most treatment works carry out a Settlement Volume Index (SVI) or Stirred Settlement Volume Index (SSVI) test manually on an almost daily basis, requiring up to 20 minutes of operator time. It is a measure of how well the Activated Sludge (treatment bacteria) will separate from the clear effluent. A poorly settling sludge is in danger of having the activated sludge wash out in the effluent stream, which may result in a number of problems.

At present, no online system exists that is able to perform SVI/SSVI measurements. It is normally either completed in laboratory or by direct measurement of blanket level in the actual clarifier. The device 100 may be operable to draw the sample into the respiration chamber (thereby mimicking actual in-plant operating conditions) and to carry out the test, measuring both settled levels and supernatant levels. The sample is allowed to settle either with no stirring (SVI) or very low stirring rate (SSVI). After an operator adjustable time (normally 30 minutes) the inner shell is raised to push the sample slowly up past the solids measuring device. As the liquid flows past the solids sensor a measure of any floating solids is performed (which typically will show fairly high levels). Secondly the solids level in the supernatant liquid is measured (which should be low) and finally the (typically very high) solids level in the settled layer is measured. The percentage of full sample height at which a sudden increase in solids layer is detected is the SVI/SSVI. Because it is known exactly where the piston is relative to the solids sensor, this can be determined using device 100. The settlement tests do not require highly accurate solids measurements as all that is of interest is the position of the gross interface. The variation in solids concentration is very large from supernatant to settle layer and device 100 enables measurement of both TSS and Settlement to be performed during a single sample ejection.

Ammonia ($NH_4$), pH and Potassium ($K^+$) Sensors

The Ammonia and Potassium sensors may be ion selective electrodes, while the pH sensor may be a glass galvanic type electrode and supplied with a reference electrode. All the sensors may be mounted on the external piston 320 of the device 100. In an embodiment, the electrodes are moulded into modules which may be "hockey puck" shaped modules 380a, 380b. These modules can be replaced without need for wiring, simply by loosening the retaining clamp and sliding out the module for replacement.

As mentioned previously, all sensing heads are cleaned each time the piston is automatically drawn up into the calibration position. Calibration fluids are drawn from reservoirs mounted on the handrail of the plant and as long as their calibration fluids are kept topped up the cleaning and calibration process is fully automatic.

The nitrification process, conversion of Ammonia ultimately to nitrate, is important in treatment system because—
1. Ammonia discharge allowances are getting ever tighter
2. It is an expensive process, requiring 4.5 times more oxygen than BOD removal.
3. The nitrifiers are highly susceptible to toxic shock loads.
4. It is a difficult process to monitor and many parameters should be optimised including
   DO Levels—should be kept high, greater than 2.5
   pH—ideally greater than 7, up to 8.5
   Nitrification should have 7 mg of Alkalinity per mg of Ammonia treated
   Temperature, greater than 12 C (a problem in winter).

The device's ammonia electrode can determine, depending on location, either
   Ammonia Loading
   Ammonia Removal Rate
   Discharge Ammonia Using the respirometry run data explained below, a measure for the Percentage Nitrification Rate Maximum may be obtained. This is a measure of bacterial nitrification health and therefore, an early warning system for chronic toxicity or shock loading. Rate of Nitrification against DO level can be used in feed forward control systems to set DO levels as low as possible for energy saving measures.

The pH sensor is a useful tool when optimising nitrification rates, while the potassium electrode is provided as Potassium can interfere with the Ammonia electrode. Additionally, temperature sensors may be provided for operator information and LDO calibration purposes.

Data Processing

That the device comprises a sealed respirometer provides the capability to draw treatment rate curves, by deliberately allowing the sample dissolved oxygen concentration to fall towards zero as part of the testing process.

Oxygen Update Rate (OUR)

This measures the level of the activity of the bacteria. The quicker the DO is removed in the sealed sample chamber, the more active the bacteria. OUR can be calculated as the rate of decrease of DO over time. Conclusions can be drawn as to what this means for influent/effluent loading. OUR is measured in milligrams of oxygen per liter of activated sludge per hour.

Specific Oxygen Update Rate (SOUR)/Sludge Health (Total)

This is a measure of bacteria health in the system. It is measured as the quantity of oxygen uptake by a fixed bacterial mass per hour. Therefore as long as the food source is in excess the only parameters which can change the measure are temperature and bacterial health. Given that temperature changes are normally fairly slow, the main cause of a change in this parameter is the health of the bacteria. As such it is a powerful measure of potential toxic conditions. In addition this measure can be used to calculate the biodegradation capacity of the system. It is measured by the formula OUR/MLSS. As the device 100 is able to measure both of these, an online measurement for SOUR is possible. This figure can then be converted into both Kgs Organic load removal and Kgs Ammonia load removal.

In a particular embodiment, the combined health of both Nitrifying and Carbonaceous bacteria may be measured.

Critical Carbonaceous DO (Cc)

Figure 8:
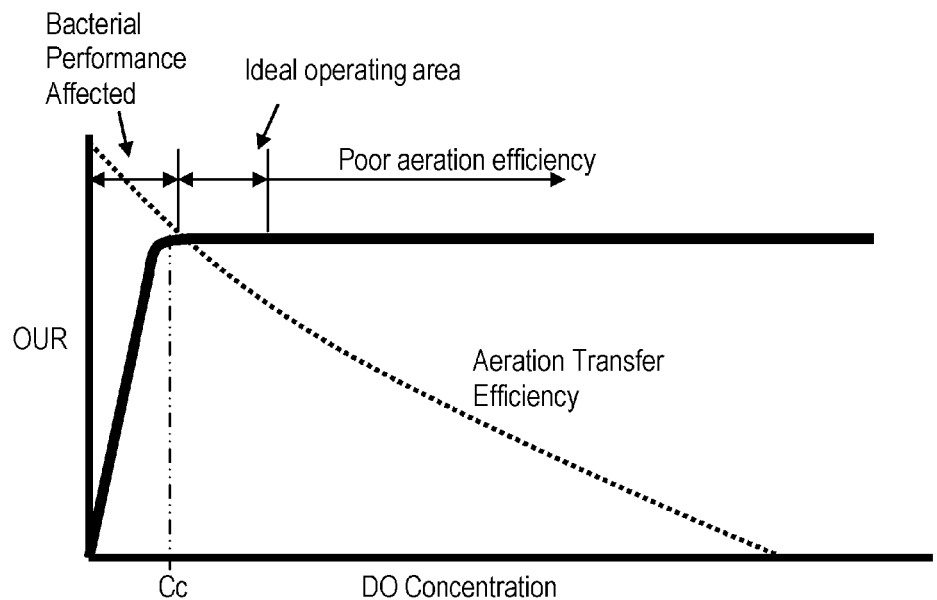
FIG. 8 is an oxygen uptake rate trace plotting activity level versus dissolved concentration, for a carbonaceous plant.

This makes it possible to determine the Dissolved Oxygen concentration at which organic removal rate is maximised. It can only be determined by dynamically assessing the rate of change of the oxygen uptake rate when compared to the dissolved oxygen level in the chamber. This can be derived from the system respiration curve. If the plant is carbonaceous (BOD removal only) an OUR trace may be used to draw activity level versus DO concentration. This is illustrated in FIG. 8.

The point at which activity dramatically decreases is called the Critical Carbonaceous DO Level (Cc). This is a very well defined point. If the plant DO is above this level the BOD removal rate is maximised. Going too far above it means the plant is running inefficiently. Running below it means BOD is not being removed as effectively as it could be. In addition running for extended periods below this critical point can lead to other problems.

4.4 Cn/Critical Nitrification Point

Figure 9:
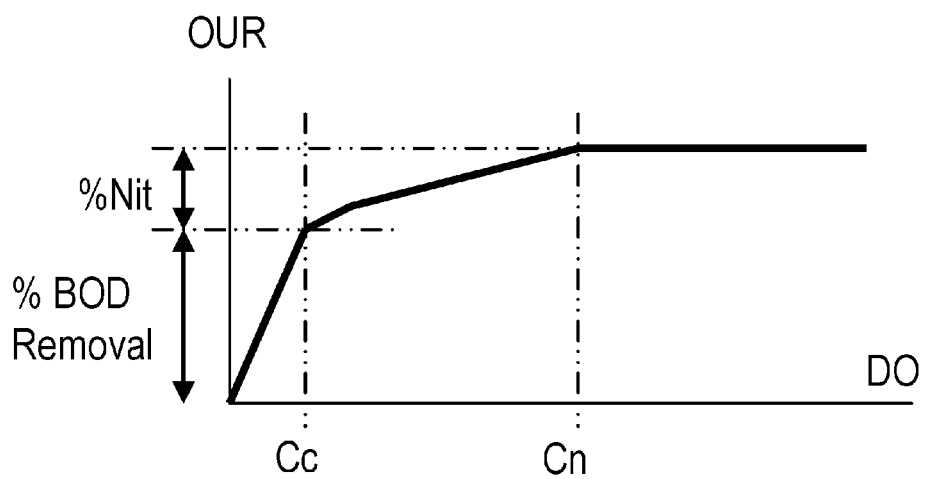
FIG. 9 is an oxygen uptake rate trace plotting activity level versus dissolved concentration, for a carbonaceous and nitrifying plant.

If the plant contains a mixture of both carbonaceous and nitrifying bacteria the graph changes shape and yields a lot more information. This is illustrated in FIG. 9. As with Cc, Cn determined by dynamically assessing the rate of change of the oxygen uptake rate when compared to the dissolved oxygen level in the chamber, derived from the system respiration curve.

Using the information contained within this graph it is possible to optimise Ammonia removal rates at minimum cost. FIG. 9 not only shows us the point at which Ammonia removal rates begins to decline Cn, it also shows the rate at which it declines compared to plant DO level. Finally the point at which the DO reaches Cc also determines the % Nitrification rate. Therefore the rate of ammonia removal can be directly related to an increase or decrease in oxygen concentration.

% Nitrification—Sludge Nitrifying Health

This is a measure of the nitrifying bacteria activity (robustness). When converted to the specific nitrifying rate it is a measure of nitrification health. It is an extension of OUR/SOUR and specifically determines the health of the Nitrifying bacteria in the treatment system. No other system automatically measures this.

This is calculated from the amount of oxygen consumed which is used for Ammonia reduction. This can be converted into Kgs of Ammonia treated per day—

$$\frac{\% \ OURforNitrification}{1000 \ F.} (mg/l/h) \cdot 24(hours) \cdot AerationVolume(m^3) = NH_4(kg/day)$$

where:
F=4.2 If the plant has an effective denitrification zone (this zone converts
$NO_3$ to $N_2$+ free oxygen.
F=4.6 If no denitrification occurs Note that this formula assumes the plant DO is above the critical nitrification DO at all times and allowances should be made if this is not the case.

By measuring the relationship and combining it with OUR+$NH_4$ readings enabling minimising of DO target set points (lower DO=less Energy)
accurate DO measurement (instrument self cleans and calibrates)
accurate nitrifying population measurement
and accurate measurement of $NH_4$ load and effluent;
a highly efficient feed forward control system is provided, as well as a feed back check system F/M Ratio This is the ratio of influent BOD to MLSS. This measure is used in treatment management.

4.7 BOD/Biological Oxygen Demand

Most BOD measurements refer to the standard BOD 5 test. This is a measure of how much oxygen would be consumed in a receiving watercourse over 5 days in breaking down the influent BOD. The test protocol normally excludes the impact of Ammonia.

The system proposed herein can provide a measure of influent loading on the treatment works—it is a very quick test and includes the effect of Ammonia. This test therefore measures the immediate or short-term loading on the plant. This is however, a highly relevant test as most treatment works have a very short hydraulic retention time (4-6 hours). If the device 100 is located at the front-end of the treatment works the OUR is directly related to the influent loading level. Particularly when the inbuilt aeration device raises the DO above the Critical Carbonaceous level a highly accurate measure of plant loading is determined. Measuring without this additional aeration could lead to significant errors in measurement.

Once the BOD and Ammonia loads have been treated the bacteria return to their starving or endogenous respiration rate. If this is converted to the specific respiration rate it will be a reliable measure of treatment completion. This can be measured if the device 100 is positioned near the end of the treatment system. The load measure is simply the actual in-situ OUR. This parameter may therefore be used interchangeably with BODst and Plant Loading.

The OUR is a measure of how active the biomass is at any point in the treatment system. Given that the MLSS or the concentration of bacteria at any point in the system does not instantaneously vary significantly, the following can be interpreted.

High OUR—high concentration of load (BOD+$NH_4$) available to the bacteria. Therefore the system is under heavy load at this point.

Low OUR—
1. BOD+$NH_4$ consumed—system clean
2. BOD removed but $NH_4$ still present—check $NH_4$ readout
3. DO is below critical operational level—check DO reading
4. Plant is suffering from toxic shock
   check DO levels
   check $NH_4$ levels All tests may be carried out wherever the devices are positioned in a treatment plant. However, it may be beneficial to perform certain tests in particular zones of the plant. Table 1 shows where it may be particularly beneficial (shown as Y) to carry out certain of the above described tests. The numbers in columns 2-4 indicate the position of the device, and stand for:
1. Inlet Respiration zone
2. Middle zone
3. Outlet zone.

TABLE 1

| Test | 1 | 2 | 3 |
|---|---|---|---|
| DO | Y | Y | Y |
| NH4 | Y | Y | Y |
| Temperature | Y | Y | Y |
| PH | — | — | Y |
| K+ | Y | Y | Y |
| MLSS | — | — | Y |
| TSS | — | — | Y |
| OUR | Y | Y | Y |
| Cc | Y | — | Y |
| Cn | Y | — | Y |
| SVI/SSVI | — | — | Y |
| % Nitrification | Y | — | Y |

Furthermore, the system is designed with bespoke software for feedback and/or feedforward control. Depending on the position of several units within the treatment system, it can be used to:
1. Measure incoming load.
2. Determine load removal rates and the required DO levels to achieve this.

3. Monitor accurately the correct treatment conditions in the treatment system.
4. Measure effluent load and feedback results to the feed forward control mechanism.

Toxicity Assessment

Toxicity Assessment cannot be simply carried out by checking the OUR rate at the inlet against the normal expected level. This is because heavy rainfall conditions could dilute the incoming food source creating a low OUR and therefore a false toxicity reading.

Therefore an assessment of whether the device 100 units are picking up a toxic effect is made on a decision matrix.

The decision matrix lists factors indicating toxicity and their relative ranking. An example may be:

| Non Toxic | | Parameter | Toxic | |
|---|---|---|---|---|
| −1 | High | OUR Rate | Low | 1 |
| −1 | Stable | % Nitrification | Reducing | 1 |
| −1 | Normal | Ammonia Reduction Rate | Low | 2 |

This data and ranking is combined to give an evaluation protocol as follows:

| Ranking | Assessment |
|---|---|
| −3 | Non Toxic |
| −2 | Non Toxic |
| −1 | No Assessment |
| 0 | No Assessment |
| 1 | No Assessment |
| 2 | Possible Nitrification Toxicity |
| 3 | Highly toxic |

Further levels of complexity can be built in to the local SCADA/PLC system. For instance if both Ammonia reduction rates and Nitrification % indicate toxicity but OUR is only slightly compromised then it is likely there is only toxicity to Nitrifiers being seen, which is possibly overridden in the OUR figure by carbonaceous improvement.

The following factors can also be utilised to check if low OUR rates noted are toxic or not.
1. Is influent Ammonia much lower than normal. This would tend to indicate that the influent levels are weak.
2. In addition an influent is normally turbid, a clear supernatant on the inlet to a domestic treatment plant would indicated weak influent strengths and this could be measured by completing an inlet TSS test.

Various improvements and modifications may be made to the above without departing from the spirit and scope of the invention. Also aspects from one embodiment will, where appropriate, be applicable to other embodiments.

The invention claimed is:

1. A wastewater monitoring device comprising:
a shell member and a piston member, wherein said piston member is configured to be located inside said shell member so as to define a selectively sealable first chamber;
a first oxygen sensor configured to measure the level of oxygen dissolved in a liquid; said first oxygen sensor configured to be located inside of the first chamber when the first chamber is sealed;
a second oxygen sensor configured to measure the level of oxygen dissolved in the wastewater being tested; and a selectively sealable second chamber, the piston member being configured to be located inside the shell member so as to define said selectively sealable second chamber;
wherein at least one of the shell member and the piston member is configured to be actuated linearly relative to the other so as to:
selectively seal said selectively sealable first chamber with the first oxygen sensor and a sample of the wastewater being tested therein;
deploy the second oxygen sensor in the wastewater being tested;
deploy the first oxygen sensor that is calibrated, into the same wastewater as the second oxygen sensor; and
selectively seal said selectively sealable second chamber.

2. A wastewater monitoring system comprising at least one wastewater monitoring device as claimed in claim 1; and a controller, wherein the wastewater monitoring system is configured to perform a first automatic calibration operation, comprising:
calibrating said first oxygen sensor within the sealed selectively sealable first chamber under controlled conditions;
actuating said at least one of said shell member and said piston member linearly relative to the other to deploy the calibrated first oxygen sensor into the same wastewater as the second oxygen sensor; and
calibrating the second oxygen sensor so that its output matches that of the first oxygen sensor.

3. A wastewater monitoring system as claimed in claim 2 wherein, to calibrate the first oxygen sensor, said first automatic calibration operation comprises:
sealing a sample of the wastewater and said first oxygen sensor within said selectively sealable first chamber;
determining that the level of dissolved oxygen is constant over time using said first oxygen sensor and, when constant, calibrating the said first oxygen sensor at zero.

4. A wastewater monitoring system as claimed in claim 2 wherein, to calibrate the first oxygen sensor, said first automatic calibration operation comprises actuating at least one of said shell member and said piston member linearly relative to the other to deploy the first oxygen sensor into an air space within the wastewater device; and measuring the level of dissolved oxygen in air using said first oxygen sensor and using this measure as a high point calibration value.

5. A wastewater monitoring system as claimed in claim 2 said device being configured to perform a further calibration operation, said further calibration operation comprising calibrating said second oxygen sensor within said sealed selectively sealable second chamber under controlled conditions.

6. A wastewater system as claimed in claim 5 being configured to compare the results of said first automatic calibration operation and said further calibration operation so as to determine whether they corroborate.

7. A wastewater monitoring system as claimed in claim 6 wherein, to calibrate the second oxygen sensor, said further calibration operation comprises measuring the level of dissolved oxygen in air using said second oxygen sensor and using this measure as a high point calibration value.

8. A wastewater monitoring system as claimed in claim 5 wherein,
to calibrate the second oxygen sensor, said further calibration operation comprises:
sealing a sample of the wastewater and said second oxygen sensor within the selectively sealable second chamber;

determining that the level of dissolved oxygen is constant over time using said second oxygen sensor and, when constant, calibrating the said second oxygen sensor at zero.

9. A wastewater monitoring system as claimed in claim 5 comprising oxygenating means for oxygenating a liquid sample contained within at least one of said first chamber and said second chamber.

10. A wastewater monitoring system as claimed in claim 2 comprising a plurality of said wastewater monitoring devices, wherein said system carries out at least one of feed forward and feed back measurement data as appropriate; measures an incoming load; determines load removal rates and the required dissolved oxygen levels to achieve this; monitors the correct treatment conditions in the treatment system; and measures effluent load and feeds back results to the controller.

11. A wastewater monitoring system as claimed in claim 1 comprising a solids sensor operable to measure a level of suspended solids within a sample, said device being configured to contain a liquid sample into the selectively sealable first chamber and to perform one or more of:
   a settled volume index measurement;
   a stirred settled volume index measurement after stirring the sample;
   a mixed liquor suspended solids measurement; and
   allow the sample to settle over a predetermined time and to perform a total suspended solids measurement on a settled supernatant layer.

12. A wastewater monitoring system as claimed in claim 1 comprising a sealed calibration housing and a reservoir for calibration fluids, and being configured to:
   withdraw one or more sensors, other than the first and second oxygen sensors, into the calibration housing, fill the calibration housing with calibration fluids, and calibrate the sensor(s) using said calibration fluids.

13. A wastewater monitoring system as claimed in claim 1 being configured to:
   seal a sample of the wastewater and said first oxygen sensor within the selectively sealable first chamber of the device;
   oxygenate the sample to raise the level of dissolved oxygen within it;
   determine the rate of change of the dissolved oxygen level over time.

14. A wastewater monitoring system as claimed in claim 1 being configured to plot the change in oxygen uptake rate against the concentration of dissolved oxygen so as to determine an optimum operating dissolved oxygen concentration range.

15. A wastewater monitoring system as claimed in claim 14 being configured to determine one or more of:
   a Critical Carbonaceous point at which decreasing dissolved oxygen concentration results in a sharp fall in the oxygen uptake rate;
   a Critical Nitrification point where increasing dissolved oxygen concentration begins to have very little or no effect on the oxygen uptake rate, this being indicative of the point at which dissolved ammonia removal rates is considered to be maximised;
   an online toxicity assessment of the wastewater under test.

16. A wastewater monitoring device as claimed in claim 1 wherein said selectively sealable first chamber and said selectively sealable second chamber are both adjacent each other within said single shell member and are separated by a seal forming part of said piston member which seals against the inside of the shell member.

17. A wastewater monitoring device as claimed in claim 1 wherein said device comprises a first actuator for the shell member and a second actuator for the piston member configured to enable each of said shell member and said piston member to be independently actuated relative to the other; and wherein said first oxygen sensor is attached to said second actuator such that it moves linearly with linear movement of said piston member.

18. A wastewater monitoring device as claimed in claim 17 wherein said shell member, piston member, first actuator, second actuator, first oxygen sensor and second oxygen sensor are all housed within a casing.

19. A wastewater monitoring device as claimed in claim 1 wherein said second oxygen sensor is comprised within a housing forming part of said piston member.

20. A wastewater monitoring device as claimed in claim 1 wherein said device is operable in at least three configurations, a first configuration in which the piston member is withdrawn relative to the shell member thereby allowing the ingress of surrounding liquid, a second configuration wherein said piston member is deployed relative to the shell member so as to contain said liquid and said first oxygen sensor within said selectively sealable first chamber, and a third configuration wherein said piston member is deployed further relative to the shell member, so as to expel the contained liquid from said selectively sealable first chamber.

* * * * *